(12) United States Patent
Butts et al.

(10) Patent No.: US 6,849,264 B2
(45) Date of Patent: Feb. 1, 2005

(54) SILICONE COMPOSITIONS FOR PERSONAL CARE PRODUCTS AND METHOD FOR MAKING

(75) Inventors: Matthew David Butts, Rexford, NY (US); Susan Adams Nye, Feura Bush, NY (US); Christopher Michael Byrne, Clifton Park, NY (US); Alan Roy Katritzky, Gainesville, FL (US); Jon Walter Merkert, Charlotte, NC (US)

(73) Assignee: General Electric Company, Niskayuna, NY (US)

( * ) Notice: Subject to any disclaimer, the term of this patent is extended or adjusted under 35 U.S.C. 154(b) by 2 days.

(21) Appl. No.: 10/270,283

(22) Filed: Oct. 15, 2002

(65) Prior Publication Data

US 2003/0086889 A1 May 8, 2003

Related U.S. Application Data

(62) Division of application No. 09/616,532, filed on Jul. 14, 2000, now Pat. No. 6,488,921.

(51) Int. Cl.$^7$ .......................... A61K 9/00; A61K 31/74; A01M 25/34
(52) U.S. Cl. ..................... 424/400; 424/402; 424/78.08
(58) Field of Search ........................... 424/20.12, 70.1, 424/401, 78.08, 402

(56) References Cited

U.S. PATENT DOCUMENTS

| | | | |
|---|---|---|---|
| 4,567,039 A | 1/1986 | Stadnick et al. | |
| 4,820,308 A | 4/1989 | Madrange et al. | |
| 4,859,460 A | 8/1989 | Mahieu et al. | |
| 4,971,786 A | 11/1990 | Grollier et al. | |
| 4,973,475 A | 11/1990 | Schnetzinger et al. | |
| 5,030,756 A | 7/1991 | Deppert et al. | |
| 5,087,733 A | 2/1992 | Deppert et al. | |
| 5,160,733 A | 11/1992 | Berthiaume | |
| 5,206,013 A | 4/1993 | Deppert et al. | |
| 5,211,942 A | 5/1993 | Deppert et al. | |
| 5,254,335 A | 10/1993 | Deppert et al. | |
| 5,350,572 A | 9/1994 | Savaides et al. | |
| 5,523,080 A | 6/1996 | Gough et al. | |
| 5,525,332 A | 6/1996 | Gough et al. | |
| 5,609,856 A | 3/1997 | Dubief et al. | |
| 5,609,861 A | 3/1997 | Dubief et al. | |
| 5,969,077 A | 10/1999 | Schrock et al. | |
| 6,488,921 B1 * | 12/2002 | Butts et al. | ................ 424/70.1 |

FOREIGN PATENT DOCUMENTS

| | | |
|---|---|---|
| EP | 0159628 | 4/1985 |
| EP | 0509922 | 4/1992 |
| WO | 9935180 | 12/1997 |
| WO | 9838974 | 4/1998 |
| WO | 0040210 | 1/2000 |
| WO | WO 00/40210 | * 7/2000 |

OTHER PUBLICATIONS

"Development of a Novel Attachable Initiator for 'Living' Radical Polymerization and Synthesis of Polysiloxane Block Copolymer", Nakagawa and Matyjaszewski, Amer. Chem. Soc., Polym. Preprints, 1996, 270–271.

* cited by examiner

*Primary Examiner*—Thurman K. Page
*Assistant Examiner*—Blessing Fubara
(74) *Attorney, Agent, or Firm*—Andrew J. Caruso; Patrick K. Patnode

(57) ABSTRACT

A composition and method for making a silicone composition is provided which comprises at least one polysiloxane or silicone resin, at least one linker, and at least one molecular hook wherein the molecular hook comprises a heterocyclic trimethylpyrimidinium compound.

17 Claims, No Drawings

SILICONE COMPOSITIONS FOR PERSONAL CARE PRODUCTS AND METHOD FOR MAKING

CROSS-REFERENCE TO RELATED APPLICATION

This application is a divisional of application Ser. No. 09/616,532, filed Jul. 14, 2000, now U.S. Pat. No. 6,488,921, which is hereby incorporated by reference in its entirety.

BACKGROUND OF THE INVENTION

The present invention relates to compositions for personal care products. More particularly, the present invention relates to silicone compositions which achieve conditioning benefits in hair care products.

Silicones are widely used in hair care products due to the conditioning benefit that they impart to hair. By modern day technology, the silicone is deposited on hair during the application process but is held only by weak physical forces, such as hydrogen bonding or van der Waals interactions. Generally, conditioning benefits are attributed to the deposition of high molecular weight, high viscosity fluids and gums which can weigh down the hair. Because the interactive forces are weak, the benefits of silicone by deposition are short lived. Beneficial conditioning effects can also be caused by treating hair with silanol capped amino-functionalized silicones. These can undergo condensation cure reactions on hair to form somewhat durable films.

It is widely known by those skilled in the art that covalent bonding is one key to "permanent" hair treatment. Processes which alter the structure of the hair, such as permanent wave and color treatment methods, do provide longer lasting effects. These processes include glycolate reduction and peroxide reoxidation. A significant disadvantage of these processes is that they are very damaging to hair and can only be carried out infrequently.

Gough et al. in U.S. Pat. Nos. 5,523,080 and 5,525,332 describe the synthesis of silicone-azlactone polymers which exhibit covalent bonding and "permanent" conditioning benefit. Gough et al. discuss incorporating an azlactone-functionalized copolymer which consists of vinylazlactone and methacryloyl polydimethylsiloxane monomers into a silicone-active group-hair structure. The hair treatment using the silicone-azlactone polymers does not consist of the steps of reduction with a glycolate or reoxidation with peroxide.

It is desirable to produce silicone compositions which can be used to treat damaged hair and provide durable benefits. Thus, silicone products are constantly being sought which can both covalently bond to hair as well as impart hair care benefits appreciated by consumers.

BRIEF SUMMARY OF THE INVENTION

The present invention provides a silicone composition which comprises at least one polysiloxane or silicone resin, at least one linker, and at least one molecular hook wherein the molecular hook comprises a heterocyclic trimethylpyrimidinium compound.

The present invention further provides a method for making a silicone composition comprising at least one polysiloxane or silicone resin, at least one linker, and at least one molecular hook. The method comprises combining a linker, a molecular hook, and a polysiloxane or silicone resin wherein the molecular hook comprises a heterocyclic trimethylpyrimidinium compound.

DETAILED DESCRIPTION OF THE INVENTION

The present invention comprises a silicone composition which includes at least one polysiloxane or silicone resin, at least one linker, and at least one molecular hook. The linker is bound to both a molecular hook and to an atom of a polysiloxane or silicone resin. Preferably the linker is bound to a polysiloxane or silicone resin through a silicon (Si), carbon (C), oxygen (O), nitrogen (N), or sulfur (S) atom, and most preferably through a silicon atom. When more than one linker is present, it is also contemplated that linkers may be bound to a polysiloxane or silicone resin through more than one type of atom, for example through both silicon and carbon atoms.

The present invention includes a silicone composition having the formula:

$$M_a M'_b D_c D'_d T_e T'_f Q_g$$

where the subscripts a, b, c, d, e, f and g are zero or a positive integer, subject to the limitation that the sum of the subscripts b, d and f is one or greater; where M has the formula:

$$R^{40}_3 SiO_{1/2},$$

M' has the formula:

$$(Z-Y)R^{41}_2 SiO_{1/2},$$

D has the formula:

$$R^{42}_2 SiO_{2/2},$$

D' has the formula:

$$(Z-Y)R^{43} SiO_{2/2},$$

T has the formula:

$$R^{44} SiO_{3/2},$$

T' has the formula:

$$(Z-Y)SiO_{3/2},$$

and Q has the formula $SiO_{4/2}$, where each $R^{40}$, $R^{41}$, $R^{42}$, $R^{43}$, $R^{44}$ is independently at each occurrence a hydrogen atom, $C_{1-22}$ alkyl, $C_{1-22}$ alkoxy, $C_{2-22}$ alkenyl, $C_{6-14}$ aryl, $C_{6-22}$ alkyl-substituted aryl, or $C_{6-22}$ aralkyl which groups may be halogenated, for example, fluorinated to contain fluorocarbons such as $C_{1-22}$ fluoroalkyl, or may contain amino groups to form aminoalkyls, for example aminopropyl or aminoethylaminopropyl, or may contain polyether units of the formula $(CH_2CHR^{45}O)_k$ where $R^{45}$ is $CH_3$ or H and k is in a range between about 4 and 20; Z, independently at each occurrence, represents a molecular hook; and Y, independently at each occurrence, represents a linker. The term "alkyl" as used in various embodiments of the present invention is intended to designate both normal alkyl, branched alkyl, aralkyl, and cycloalkyl radicals. Normal and branched alkyl radicals are preferably those containing in a range between about 1 and about 12 carbon atoms, and include as illustrative non-limiting examples methyl, ethyl, propyl, isopropyl, butyl, tertiary-butyl, pentyl, neopentyl, and hexyl. Cycloalkyl radicals represented are preferably those containing in a range between about 4 and about 12 ring carbon atoms. Some illustrative non-limiting examples of these cycloalkyl radicals include cyclobutyl, cyclopentyl, cyclohexyl, methylcyclohexyl, and cycloheptyl. Preferred aralkyl radicals are those containing in a range between about 7 and about 14 carbon atoms; these include, but are not limited to, benzyl, phenylbutyl, phenylpropyl, and phenylethyl. Aryl radicals used in the various embodiments of the present invention are preferably those containing in a range between about 6 and about 14 ring carbon atoms. Some illustrative non-limiting examples of these aryl radicals include phenyl, biphenyl, and naphthyl. An illustrative non-limiting example of a halogenated moiety suitable is trifluoropropyl.

The polysiloxanes or silicone resins of the present invention are typically prepared by the hydrosilylation of an organohydrogen silicone having the formula:

$$M_a M^H_b D_c D^H_d T_e T^H_f Q_g$$

where the subscripts a, b, c, d, e, f and g are zero or a positive integer, subject to the limitation that the sum of the subscripts b, d and f is one or greater; M, D, T and Q are defined as above;

$M^H$ has the formula:

$$R^{41}_{3-h} H_h SiO_{1/2},$$

$D^H$ has the formula:

$$H_{2-i} R^{43}_i SiO_{2/2},$$

$T^H$ has the formula:

$$HSiO_{3/2},$$

where each $R^{41}$ and $R^{43}$ is independently as defined above; subscript h is in a range between 1 and 3; and subscript i is 0 or 1.

Hydrosilylation is typically accomplished in the presence of a suitable hydrosilylation catalyst. The catalysts preferred for use with these compositions are described in U.S. Pat. Nos. 3,715,334; 3,775,452; and 3,814,730 to Karstedt. Additional background concerning the art may be found at J. L. Spier, "Homogeneous Catalysis of Hydrosilation by Transition Metals, in *Advances in Organometallic Chemistry*, volume 17, pages 407 through 447, F. G. A. Stone and R. West editors, published by the Academic Press (New York, 1979). A preferred catalyst contains platinum. Persons skilled in the art can easily determine an effective amount of platinum catalyst. Generally, an effective amount is in a range between about 0.1 parts per million and about 50 parts per million of the total silicone composition composition.

The organohydrogen silicone compounds that are the precursors to the compounds of the present invention may be prepared by the process disclosed in U.S. Pat. No. 5,420, 221. The '221 patent discloses the redistribution of polydimethylsiloxane polymers with organohydrogen silicone polymers and optionally, added chain stopper, to provide a silicone with randomly-distributed hydride groups using a Lewis acid catalyst, preferably a phosphonitrilic compound.

Synthesis of the polysiloxane or silicone resin may also be performed by other method known to those skilled in the art, for example, the hydrosilylation of a monomer such as methyldichlorosilane could be followed by co-hydrolysis with the appropriate dialkyldichlorosilane and optionally, chlorotrimethylsilane.

It is to be noted that as pure compounds, the subscripts describing the organohydrogen siloxane precursor and the hydrosilylation adduct of the present invention are integers as required by the rules of chemical stoichiometry. The subscripts will assume non-integral values for mixtures of compounds that are described by these formulas. The restrictions on the subscripts heretofore described for the stoichiometric subscripts of these compounds are for the pure compounds, not the mixtures.

In specific embodiments of the present invention, the silicone composition typically comprises at least one compound of the following formulas, (I), (II), (III), (IV), (V), (VI), or (VII):

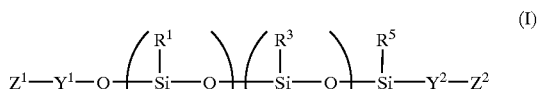

(I)

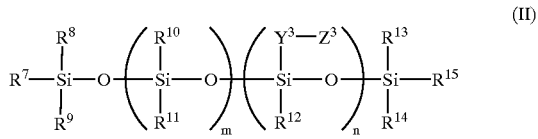

(II)

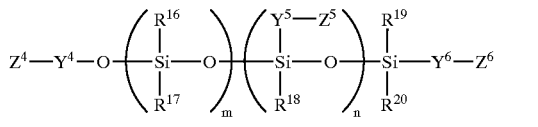

(III)

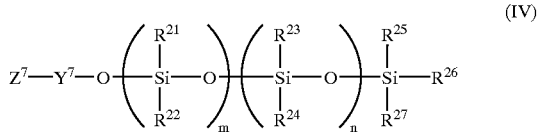

(IV)

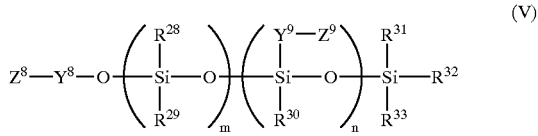

(V)

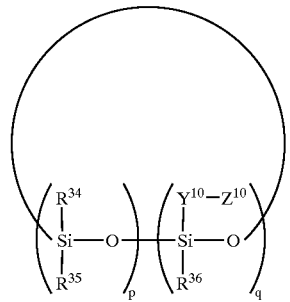

(VI)

$$(R^{37}_3 SiO_{1/2})_a [(Z-Y)R^{38}_2 SiO_{1/2}]_b (SiO_{4/2})_g \qquad (VII)$$

where each $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, and $R^{38}$ is independently at each occurrence a hydrogen atom, $C_{1-22}$ alkyl, $C_{1-22}$ alkoxyl, $C_{2-22}$ alkenyl, $C_{6-14}$ aryl, $C_{6-22}$ alkyl-substituted aryl, or $C_{6-22}$ aralkyl which groups may be halogenated, for example, fluorinated to contain fluorocarbons such as $C_{1-22}$ fluoroalkyl, may contain amino groups to form aminoalkyls, or may contain polyether units; Z, $Z^1$–$Z^{10}$, independently at each occurrence, represents a molecular hook; and Y, $Y^1$–$Y^{10}$, independently at each occurrence, represents a linker; wherein "m" in each formula has a value in a range between about 0 and about 13,000, preferably about 0 and about 1000, more preferably between about 1 and about 250, still more preferably between about 5 and about 250, even more preferably between about 10 and about 150, and most preferably between about 20 and about 120; "n" in each formula h as a value in a range between about 0 and about 13,000, more preferably between about 0 and about 50, more preferably between about 1 and about 20, still more preferably between about 2 and about 10, and most preferably between about 2 and about 5 with the proviso that in formula (II) "n" is not 0; "m+n" in each formula has a value in a range between about 1 and about 26,000, preferably in a range between about 3 and about 250, and more preferably between about 5 to about 150; "q" has a value of at least one and "p+q" has a value of at least 3, preferably in a range between about 3 and about 20, more preferably in a range between about 3 and about 10, and most preferably in a range between about 3 and 6. $R^{1-38}$ is preferably methyl. The preferred silicone composition includes a compound of the formula (I) or (II). The polysiloxane or silicone resin typically has a molecular weight in a range between about 100 and about 6,000,000, preferably in a range between about 250 and about 50,000, more preferably in a range between about 500 and about 25,000, and most preferably in a range between about 500 and about 15,000.

The number of Y-Z moieties on a polysiloxane or silicone resin in the composition is at least one. In preferred embodiments the average number of Y-Z moieties on a polysiloxane or silicone resin is in a range between about 1 and about 100, more preferably in a range between about 1 and about 20, still more preferably in a range between about 1 and about 10.

In one embodiment of the present invention a polysiloxane- or silicone resin-containing composition includes a preponderance of a specific linear, branched, cross-linked, or cyclic polysiloxane or silicone resin. In other embodiments of the present invention, a polysiloxane- or silicone resin-containing composition comprises a mixture of polysiloxanes, mixture of silicone resins, or mixtures of polysiloxanes and silicone resins which may include linear, branched, cross-linked, and cyclic species. Also, suitable compositions may comprise one or more polysiloxanes, silicone resins, and mixtures thereof which may contain adventitious amounts of other species, for example, arising during the synthesis process for said polysiloxanes or silicone resins, for example at a level in a range between about 0.0001 wt. % and about 5 wt. % based on total silicon-containing species. In illustrative examples, suitable compositions may contain adventitious amounts of $D_4$, or species containing Si—H, Si—OH, Si—O-alkyl bonds, and mixtures thereof.

The molecular hook is a heterocyclic trimethylpyrimidinium compound of the formula (VIII):

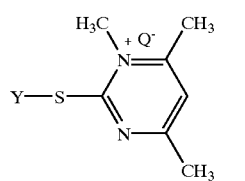

(VIII)

wherein Y represents a linker and $Q^-$ represents a counterion.

The counterion, $Q^-$, can include halides, borates, phosphates, tosylates, mesylates, triflates, and other counterions known to those skilled in the art. $Q^-$ is preferably iodide, chloride, or bromide.

The linker comprises any $C_1$–$C_{100}$ alkyl, aryl, or alkylaryl group where the $C_{1-100}$ group can be interrupted by or substituted with aromatic groups or aromatic-containing groups. The $C_{1-100}$ group may also contain one or more heteroatoms such as O, N, or S. Furthermore, the $C_{1-100}$ group may be unsubstituted or substituted with heteroatoms such as halogen. Typically, the linker has the formulas (IX) through (XV):

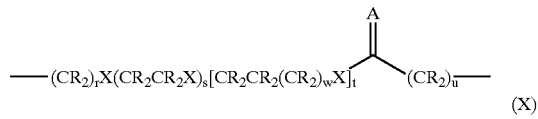

(IX)

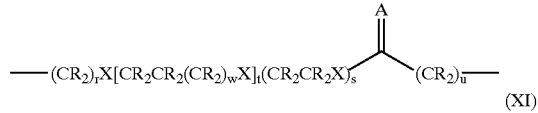

(X)

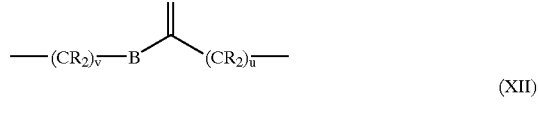

(XI)

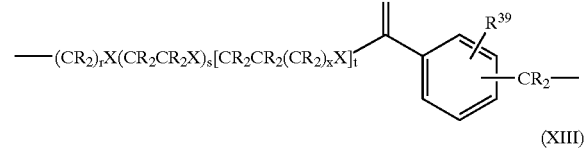

(XII)

(XIII)

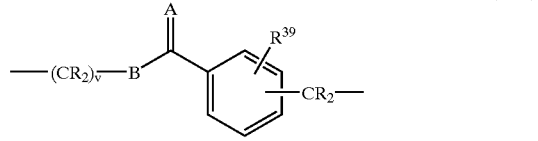

(XIV)

(XV)

where
r is in a range between about 1 and about 10, preferably 2 or 3;
s is in a range between about 0 and about 100, preferably 4 to 20;
t is in a range between about 0 and about 100, preferably in a range between about 0 and about 20, and most preferably 0;
u is in a range between about 1 and about 10, preferably 1;
v is in a range between about 1 and about 10, preferably 2 or 3;
w is 1 or 2;
x is 1 or 2;
X is O, NOH, NOR, or NR, preferably O;
wherein R is independently at each occurrence hydrogen (H), $C_{1-22}$ alkyl, $C_{1-22}$ alkoxy, $C_{2-22}$ alkenyl, $C_{6-14}$ aryl, $C_{6-22}$ alkyl-substituted aryl, or $C_{6-22}$ aralkyl where the C can be unsubstituted or substituted with heteroatoms such as oxygen (O), nitrogen (N), sulfur (S) or halogen;

wherein $R^{39}$ is independently at each occurrence hydrogen (H), $C_{1-22}$ alkyl, $C_{1-22}$ alkoxy, $C_{2-22}$ alkenyl, $C_{6-14}$ aryl, $C_{6-22}$ alkyl-substituted aryl, $C_{6-22}$ aralkyl, or fused ring system which may or may not be fused to the phenyl group where the C can be unsubstituted or substituted with heteroatoms such as O, N, S or halogen. $R^{39}$ is preferably H. If $R^{39}$ represents an aryl group, it can be fused to the ring in Formulas (XII) through (XV);

A is O, NOH, NOR, NR or S, preferably O;

B is O, NOH, NOR, NR or S, preferably O or NR and most preferably O;

and where the polysiloxane or the silicone resin is bound to the $(CR_2)_t$ (Formula IX, X, XII, and XIII), $(CR_2)_v$ (Formula XI and XIV), or $(CR_2)_w$ (Formula XV). Any of the linker structures shown in Formulas (IX) through (XV) can also be interrupted with cycloaliphatic rings or aromatic rings. Substituents on the phenyl group of formulas (XII), (XIII), (XIV), and (XV) may be present at any free valence site. The polysiloxane or silicone resin may or may not contain other functionalities by substitution at silicon atoms either the same as or distinct from those bound to the linking groups described above, such as amine-, polyether-, alkyl-, or heteroalkyl-containing groups.

The linker is typically derived from a polysiloxane or silicone resin bound linker precursor which comprises a linker bound to a leaving group. Illustrative leaving groups include halides such as chloride, bromide and iodide; tosylate, mesylate, phosphate; cyclic leaving groups (that is, those in which the leaving group remains bound in the linker) such as epoxy or other cyclic leaving group containing at least one heteroatom; and other leaving groups known to those skilled in the art, Preferred leaving groups are bromide, chloride, and iodide. In synthesis, the leaving group is replaced by a molecular hook, so that the linker becomes bound to a molecular hook.

The method for making the silicone compositions of the present invention includes combining a molecular hook, a polysiloxane or silicone resin, and a linker. The sequence of addition can be varied, for example, the linker and the molecular hook can be combined and this combination can be sequentially combined with a polysiloxane or a silicone resin. Preferably, the linker is combined with a polysiloxane or silicone resin and the combination is sequentially combined with the molecular hook.

Silicone compositions of the present invention which include at least one polysiloxane or silicone resin, at least one linker, and at least one molecular hook typically impart cosmetic and other durable benefits in products such as hair care products, but also including, textile care products, cosmetic products, oral care products, and animal care products. A particular advantage of the present invention is that many of the described linkers provide solubility, in consumer relevant media, to the silicone composition as well as the potential for additional hair care benefits which may or may not be typically associated with the functional groups of the linker. In particular, the molecular hook of the present invention is thermally and hydrolytically stable.

In hair care applications, the silicone compositions can be delivered to the hair in any appropriate formulation, for example, water or water and alcohol mixtures which can contain in a range between about 1% by weight and about 99% by weight alcohol based on the total formulation.

In order that those skilled in the art will be better able to practice the invention, the following examples are given by way of illustration and not by way of limitation.

In the following examples, $D^{R1}$ through $D^{R4}$ are defined as:

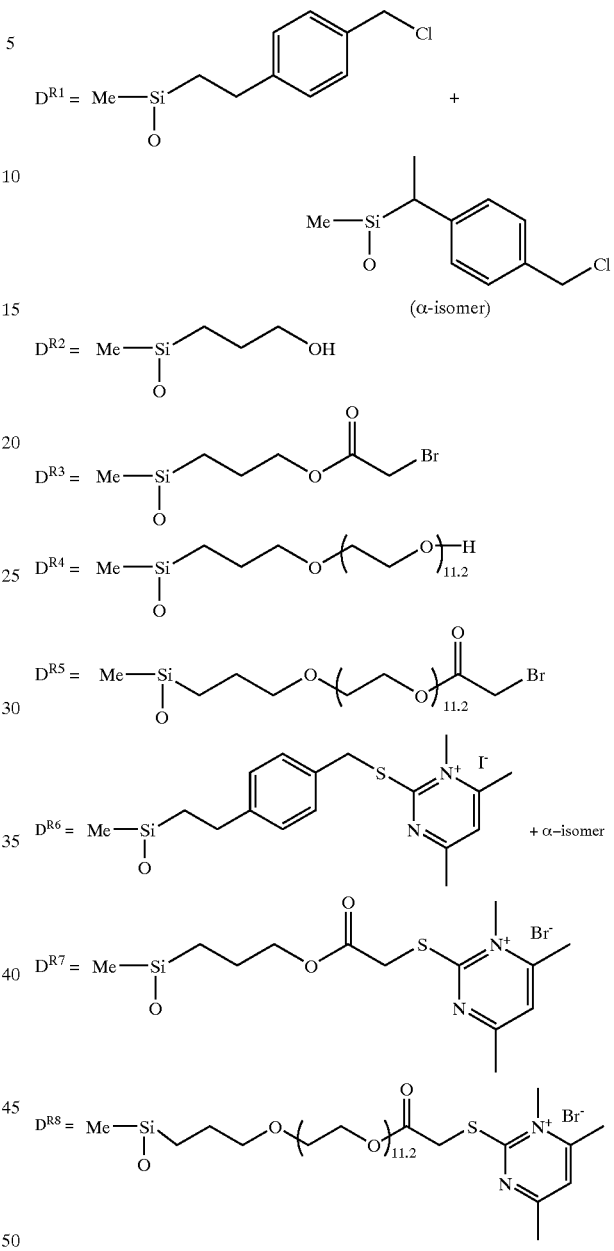

EXAMPLE 1

Silicone hydride fluid ($MD_{48}D^H{}_3M$). A 1000 milliliter three-neck round bottom flask equipped with a mechanical stirrer, thermometer attached to a temperature controlling device and a drying tube was charged with a silanol-terminated polydimethylsiloxane polymer (535.1 grams, 7.23 moles dimethylsiloxy groups), a silicone hydride fluid ($MD^H{}_xM$, 30.35 grams=0.48 moles methylhydridosiloxy groups+0.019 moles trimethylsiloxy groups), hexamethyldisiloxane (24.41 grams, 0.3 moles trimethylsiloxy groups) and a linear phosphonitrilo catalyst (2.95 grams of a 2% solution in silicone fluid, 100 parts per million). The mixture was stirred at 90° C. for two hours after which it was cooled and treated with magnesium oxide (1 gram, 0.0256 moles). The mixture was filtered through Celite to furnish the product as a clear, colorless fluid with viscosity of 58.8 centistokes and hydride level of 828 parts per million. $^1$H NMR (acetone-$d_6$): δ 4.74 (s, 3.0H, SiH), 0.12 (m, 315.0H, SiCH$_3$).

EXAMPLE 2

Benzylchloride-substituted silicone polymer (MD$_{48}$D$^{R1}_3$M). A 5 liter three-neck round bottom flask equipped with a stirbar, thermometer attached to a temperature controlling device, addition funnel and a condenser with a drying tube was charged with the silicone hydride polymer (MD$_{48}$D$^H_3$M, 931.2 grams, 0.77 moles hydride), 4-vinylbenzyl chloride (7.56 grams, 0.050 moles), di-t-butylphenol (0.52 grams) and Karstedt's catalyst (95.3 mg of a 10% Pt solution of GE Silicones Product M$^{Vi}$M$^{Vi}$ as solvent). The mixture was heated to 60° C. and additional 4-vinylbenzyl chloride (110.16 grams, 0.72 moles) was added over 60 minutes with a slight exotherm to 80° C. The reaction was followed by gasiometric hydride analysis and was finished within 6 hours after the addition was complete. The reaction mixture was heated at 130° C. under vacuum to remove unreacted volatile compounds to provide a product with viscosity of 124 centistokes. $^1$H N (acetone-$d_6$): δ 7.33 (m, 6.0H, phenyl), 7.22 (m, 6.0H, phenyl), 4.66 (s, 6.0H, CH$_2$Cl), 2.73 (m, 6.0H, SiCH$_2$CH$_2$Ar), 2.24 (m, 3.0H, SiCH(CH$_3$)Ar), 1.39 (m, 9.0H, SiCH(CH$_3$)Ar), 0.93 (m, 6.0H, SiCH$_2$CH$_2$Ar), 0.12 (m, 315H, SiCH$_3$).

EXAMPLE 3

Hydroxypropyl-substituted silicone (MD$_{45}$D$^{R2}_{3.5}$M). A 2000 milliliter three-neck round bottom flask equipped with a stirbar, thermometer attached to a temperature controlling device, addition funnel, and a condenser with a drying tube was charged with allyl alcohol (76.0 milliliters, 64.90 grams, 1.12 moles), 2-propanol (160 grams), and Karstedt's catalyst (706.8 milligrams of a 1% Pt solution in 2-propanol, 11 parts per million Pt). The solution was heated to 85° C., and silicone hydride polymer MD$_{45}$D$^H_{3.5}$M (600 grams, 0.557 moles hydride) was added over 120 minutes. The reaction was followed by gasiometric hydride analysis and was finished within 6 hours after the addition was complete. The 2-propanol was removed at 90° C. in vacuo to provide a light tan silicone polyether fluid with viscosity of 170 centistokes. $^1$H NMR (acetone-$d_6$): δ 3.50 (t, 7.0H, SiCH$_2$CH$_2$CH$_2$OH), 1.60 (m, 7.0H, SiCH$_2$CH$_2$CH$_2$O), 0.58 (m, 7.0H, SiCH$_2$CH$_2$CH$_2$O), 0.12 (m, 298.5H, SiCH$_3$).

EXAMPLE 4

Silicone with bromo-acetylated propyl substituents (MD$_{45}$D$^{R3}_{3.5}$M). A 500 milliliter three-neck round bottom flask equipped with a stirbar, thermometer attached to a temperature controlling device, Dean-Stark trap with a condenser and a drying tube was charged with bromoacetic acid (35.42 grams, 0.255 moles), Isopar C (Exxon Product, 280 grams), and the silicone hydroxypropyl fluid MD$_{45}$D$^{R2}_{3.5}$M (300.0 grams, 0.268 equivalents hydroxy groups). The reaction mixture was sparged with nitrogen for 30 minutes at ambient temperature to remove the dissolved air. para-Toluenesulfonic acid (2.50 grams, 13.1 millimoles) was added and the reaction mixture was heated to 100° C. Water and Isopar C were collected in the Dean-Stark trap. After two hours, the theoretical amount of water was obtained (4.1 grams), and the reaction mixture was cooled to ambient conditions. Excess sodium carbonate was added to neutralize the reaction, and the salts were removed by filtration through Celite after at least two hours of stirring. The volatile materials were removed under vacuum to give 324.2 grams of product (98% yield). $^1$H NMR (acetone-$d_6$): δ 4.12 (t, 7.0H, CH$_2$CH$_2$OC(O)), 3.99 (s, 7.0H, CH$_2$Br), 1.76 (m, 7.0H, SiCH$_2$CH$_2$CH$_2$O), 0.63 (m, 7.0H, SiCH$_2$CH$_2$CH$_2$O), 0.12 (m, 298.5H, SiCH$_3$).

EXAMPLE 5

Polyether-substituted silicone polymer (MD$_{52.7}$D$^{R4}_{3.3}$M). A 1000 milliliter three-neck round bottom flask equipped with a stirbar, thermometer attached to a temperature controlling device, addition funnel and a condenser with a drying tube was charged with an allyl-started poly(oxyethylene) (176.47 grams, 0.329 moles), 2-propanol (119.0 grams) and Karstedt's catalyst (86.6 milligrams of a 10% Pt solution with GE Silicones Product M$^{Vi}$M$^{Vi}$ as solvent). The solution was heated to 88° C., and the silicone hydride polymer MD$_{52.7}$D$^H_{3.3}$M (300.0 grams, 0.2917 moles hydride, prepared by the same method as described above) was added over 90 minutes. The reaction was followed by gasiometric hydride analysis and was finished within 4 hours after the addition was complete. The volatile materials including 2-propanol were removed at 90° C. under vacuum to provide a light tan silicone polyether fluid with viscosity of 1336 centistokes. $^1$H NMR (acetone-$d_6$): δ 3.85 (m, 6.6H, CH$_2$CH$_2$OH), 3.74 (m, 6.6H, CH$_2$CH$_2$OH), 3.57 (s, 132.7H, OCH$_2$CH$_2$O), 3.41 (m, 6.6H, SiCH$_2$CH$_2$CH$_2$O), 1.63 (m, 6.6H, SiCH$_2$CH$_2$CH$_2$O), 0.58 (m, 6.6H, SiCH$_2$CH$_2$CH$_2$O), 0.12 (m, 344.1H, SiCH$_3$).

EXAMPLE 6

Silicone polymer with bromo-acetylated polyether substituents (MD$_{52.7}$D$^{R5}_{3.3}$M). A 1000 milliliter three-neck round bottom flask equipped with a stirbar, thermometer attached to a temperature controlling device and a Dean-Stark trap with a condenser and a drying tube was charged with bromoacetic acid (34.00 grams, 0.245 moles), Isopar C (Exxon Product, 314 grams) and the polyether-substituted silicone MD$_{52.7}$D$^{R4}_{3.3}$M (397.50 grams, 0.257 equivalents hydroxy groups). The reaction mixture was sparged with nitrogen for 20 minutes at ambient temperature to remove the dissolved air. para-Toluenesulfonic acid (2.36 grams, 13.7 millimoles) was added, and the reaction mixture was heated to 100° C. Water and Isopar C were collected in the Dean-Stark trap. After two hours, 98% of the theoretical amount of water was obtained (4.4 grams), and the reaction mixture was cooled to ambient conditions. Potassium carbonate (3.80 grams, 27.6 millimoles) was added to neutralize the reaction, and the salts were removed by filtration through Celite after at least two hours of stirring to provide product with viscosity of 1843 centistokes. $^1$H NMR (acetone-$d_6$): δ 4.27 (m, 6.6H, CH$_2$CH$_2$OC(O)), 4.04 (s, 6.6H, CH$_2$Br), 3.70 (m, 6.6H, OCH$_2$CH$_2$OC(O)), 3.58 (s, 132.7H, OCH$_2$CH$_2$O), 3.41 (m, 6.6H, SiCH$_2$CH$_2$CH$_2$O), 1.63 (m, 6.6H, SiCH$_2$CH$_2$CH$_2$O), 0.58 (m, 6.6H, SiCH$_2$CH$_2$CH$_2$O), 0.12 (m, 344.1H, SiCH$_3$).

EXAMPLE 7

Trimethylpyrimidinium-substituted silicone polymer (MD$_{48}$D$^{R6}_3$M). To a 500 milliliter round bottom flask containing a stir bar was added 151.2 grams (36.543 millimoles) of the benzylchloride-substituted silicone polymer MD$_{45}$D$^{R1}_3$M. Sodium iodide (15.30 grams, 102.1 millimoles) was added as a solid with 200 milliliters of acetone. This mixture was allowed to stir while 15.69 grams (101.7 millimoles) of 1,4,6-trimethylpyrimidine-2-thione were added in portions as a solid. An additional 300 milliliters of acetone was then added to the pale yellow reaction mixture which was allowed to stir for 24 hours at room temperature. After this time, the reaction mixture was vacuum filtered to remove solids. The volatile materials were removed from the filtrate under vacuum. The final product was isolated in 98.7% yield (163.2 grams) as a clear, light yellow, rubbery solid. $^1$H NMR (acetone-$d_6$): δ 7.91 (s, 3.0H, pyH), 7.47 (m, 6.0H, phenyl), 7.21 (m, 6.0H, phenyl), 4.73 (s, 6.0H, CH$_2$S), 4.14 (s, 9.0H, NCH$_3$), 2.95 (s, 9.0H, 6-arylCH$_3$), 2.75 (s, 9.0H, 4-arylCH$_3$), 2.71 (m, 6.0H, SiCH$_2$CH$_2$), 2.22 (m, 3.0H, SiCH(CH$_3$)), 1.39 (d, 9.0H, SiCH(CH$_3$)), 0.93 (m, 9.0H, SiCH$_2$CH$_2$Ar), 0.12 (s, 315H, SiCH$_3$).

EXAMPLE 8

Trimethylpyrimidinium-substituted silicone polymer (MD$_{45}$D$^{R7}{}_{3.5}$M). A flask was charged with 35.0 grams (8.0 millimoles) of the silicone polymer MD$_{45}$D$^{R3}{}_{3.5}$M followed by 50 milliliters of acetone. Following the addition of 3.54 grams of 1,4,6-trimethyl-pyrimidine-2-thione (22.7 millimoles), the suspension was left stirring for six hours, whereupon starting material still remained by $^1$H NMR. After the addition of four mole percent additional thione, the mixture was left stirring overnight. The following morning, the mixture was centrifuged to remove the solid salts remaining, and the product solution was decanted and concentrated, affording 37.8 grams (87% yield) of polymer product. $^1$H NMR (acetone-$d_6$): δ 8.03 (m, 3.5H, pyH), 4.39 (s, 7.0H, CH$_2$S), 4.26 (m, 10.5H, NCH$_3$, 4.14 (t, 7.0H, CH$_2$CH$_2$CH$_2$OC(O)), 3.02 (s, 7.0H, pyCH$_3$), 2.67 (s, 7.0H, pyCH$_3$), 1.78 (m, 7.0H, CH$_2$CH$_2$CH$_2$OC(O)), 0.63 (t, 7.0H, CH$_2$CH$_2$CH$_2$OC(O)), 0.12 (m, 297H, SiMe).

EXAMPLE 9

Trimethylpyrimidinium-substituted polyether silicone polymer (MD$_{53}$D$^{R8}{}_{3.3}$M). A flask was charged with 33.5 grams (5.53 millimoles) of the silicone polymer MD$_{53}$D$^{R5}{}_{3.3}$M. Acetone (50 milliliters) was added followed by 2.90 grams of 1,4,6-trimethyl-pyrimidine-2-thione (22.7 millimoles). The suspension was allowed to stir for 1.5 hours, after which 0.08 mole percent of excess thione remained by $^1$H NMR spectroscopy. After the addition of 1.97 grams (0.325 millimoles) more silicone polymer, the mixture was left stirring overnight. The mixture was then centrifuged to remove the solid salts remaining, and the product solution was decanted. The volatile materials were removed under vacuum affording 32.6 grams (86% yield) of polymer product. $^1$H NMR (acetone-$d_6$): δ 7.96 (m, 3.5H, pyH), 4.38 (s, 7.0H, CH$_2$S), 4.26 (m, 17.5H, NCH$_3$, OCH$_2$CH$_2$OC(O)), 3.70 (m, 7H, CH$_2$OCH$_2$CH$_2$OC(O)), 3.58 (m, 142.8H, OCH$_2$CH$_2$O), 3.39 (t, 7.0H, SiCH$_2$CH$_2$CH$_2$O), 3.00 (s, 7H, pyCH$_3$), 2.68 (s, 7H, pyCH$_3$), 1.62 (m, 7.0H, SiCH$_2$CH$_2$CH$_2$O), 0.58 (m, 7.0H, SiCH$_2$CH$_2$CH$_2$O), 0.12 (s, 344H, SiCH$_3$).

It should be noted that while most reactions in which cationic polymers were made were performed at room temperature, in most instances they can be heated to speed the reaction.

EXAMPLE 10–11

Using the same procedures as described above for the structurally analogous polymers, the following materials were also synthesized:

MD$_{99}$D$^{R6}{}_3$M

M$^{R6}$D$_{48}$M$^{R6}$

Silicone deposition. Polymers described in this invention impart durable benefits to hair such as good combability, manageability, etc. The degree to which the new silicone materials interact with hair durably, after repeated shampooing, was measured. Hair switches were treated, extracted and shampooed 20 times with a commercially available shampoo (Prell®) and were then analyzed for silicon by x-ray fluorescence (XRF). The counts were converted to parts per million silicon deposition using standard methods.

TABLE 1

XRF data collected on hair switches treated with new silicone polymers after extraction and 20 shampoos with Prell ®.

| Switches | Polymer | Solvent (EtOH/water) | pH | Treatment Time (min) | Silicone Deposition (ppm)[1] |
|---|---|---|---|---|---|
| 1–3 | MD$_{48}$D$^{R6}{}_3$M | 90/10 | 7 | 5 | 1355 |
| 4–6 | MD$_{48}$D$^{R6}{}_3$M | 90/10 | 7 | 30 | 1549 |
| 7–9 | MD$_{48}$D$^{R6}{}_3$M | 90/10 | 9.5 | 5 | 4318 |
| 10–12 | MD$_{48}$D$^{R6}{}_3$M | 90/10 | 9.5 | 30 | 3803 |
| 13–15 | MD$_{99}$D$^{R6}{}_3$M | 90/10 | 7 | 5 | 1309 |
| 16–18 | MD$_{99}$D$^{R6}{}_3$M | 90/10 | 7 | 30 | 1860 |
| 19–21 | MD$_{99}$D$^{R6}{}_3$M | 90/10 | 9.5 | 5 | 2030 |
| 22–24 | MD$_{99}$D$^{R6}{}_3$M | 90/10 | 9.5 | 30 | 2391 |
| 25–27 | MD$_{99}$D$^{R6}{}_3$M | 90/10 (buffered)[2] | 9.5 | 30 | 2867 |
| 28–30 | MD$_{45}$D$^{R7}{}_{3.5}$M | 90/10 | 7 | 5 | 951 |
| 31–33 | MD$_{45}$D$^{R7}{}_{3.5}$M | 90/10 | 7 | 30 | 1349 |
| 34–36 | MD$_{45}$D$^{R7}{}_{3.5}$M | 90/10 | 9.5 | 5 | 2619 |
| 37–39 | MD$_{45}$D$^{R7}{}_{3.5}$M | 90/10 | 9.5 | 30 | 3281 |
| 40–42 | MD$_{45}$D$^{R7}{}_{3.5}$M | 90/10 (buffered)[2] | 9.5 | 30 | 9254 |

[1]Reported values are the average of measurements taken on three different hair switches treated under the same conditions.
[2]Amino methylpropanol.

Control experiments on hair switches treated with a polysiloxane without the linker and molecular hook (polydimethylsiloxane with a viscosity of 350 centistokes) for 5 minutes showed an initial deposition level of silicon as 2050 parts per million by XRF. Measurements showed that after 8 shampoos, no silicon remained on the hair. The data in Table 1 clearly show that the silicone polymers of the present invention which provide conditioning benefits, do adhere to the hair with unexpected durability.

While typical embodiments have been set forth for the purpose of illustration, the foregoing description should not be deemed to be a limitation on the scope of the invention. Accordingly, various modifications, adaptations, and alternatives may occur to one skilled in the art without departing from the spirit and scope of the present invention.

What is claimed is:

1. A silicone composition which comprises at least one polysiloxane or silicone resin, at least one linker, and at least one molecular hook wherein the molecular hook comprises a heterocyclic trimethylpyrimidinium compound, and wherein the silicone composition is included in a textile care product.

2. The composition in accordance with claim 1, wherein the heterocyclic trimethylpyrimidinium compound comprises the formula (VIII):

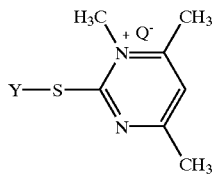

(VIII)

wherein Y represents a linker and Q⁻ represents a counterion.

3. The composition in accordance with claim 2, wherein Q⁻, is selected from the group consisting of halides, borates, phosphates, tosylates, mesylates, and triflates.

4. The composition in accordance with claim 1, wherein the at least one linker is bound to a polysiloxane or silicone resin through a silicon, carbon, oxygen, nitrogen, or sulfur atom.

5. The composition in accordance with claim 4, wherein the at least one linker is bound to a polysiloxane or silicone resin through a silicon atom.

6. The composition in accordance with claim 1, having the formula:

$$M_a M'_b D_c D'_d T_e T'_f Q_g$$

where the subscripts a, b, c, d, e, f and g are zero or a positive integer, subject to the limitation that the sum of the subscripts b, d and f is one or greater; where M has the formula:

$$R^{40}{}_3SiO_{1/2},$$

M' has the formula:

$$(Z-Y)R^{41}{}_2SiO_{1/2},$$

D has the formula:

$$R^{42}{}_2SiO_{2/2},$$

D' has the formula:

$$(Z-Y)R^{43}SiO_{2/2},$$

T has the formula:

$$R^{44}SiO_{3/2},$$

T' has the formula:

$$(Z-Y)SiO_{3/2},$$

and Q has the formula $SiO_{4/2}$, where each $R^{40}$, $R^{41}$, $R^{42}$, $R^{43}$, $R^{44}$ is independently at each occurrence a hydrogen atom, $C_{1-22}$ alkyl, $C_{1-22}$ alkoxy, $C_{2-22}$ alkenyl, $C_{6-14}$ aryl, $C_{6-22}$ alkyl-substituted aryl, $C_{6-22}$ aralkyl, $C_{1-22}$ fluoroalkyl, $C_{1-22}$ polyether, or $C_{1-22}$ amino alkyl; each Z, independently at each occurrence, is a molecular hook; and each Y, independently at each occurrence, is a linker.

7. The composition of claim 6 in which the average number of Y-Z moieties on the polysiloxane or silicone resin is between about 1 and about 100.

8. The composition of claim 7 in which the average number of Y-Z moieties on the polysiloxane or silicone resin is between about 1 and about 10.

9. The composition in accordance with claim 6 comprising at least one compound of the following formulas, (I), (II), (III), (IV), (V), (VI), or (VII):

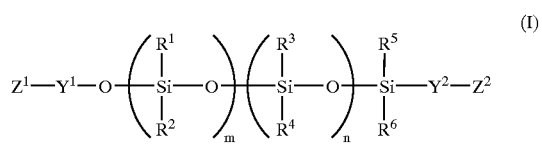

(I)

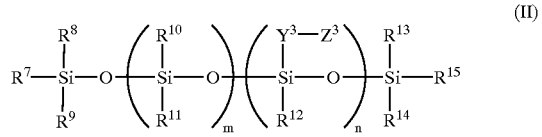

(II)

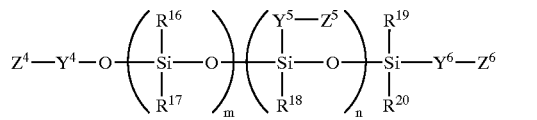

(III)

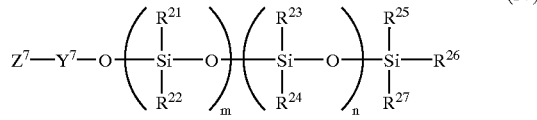

(IV)

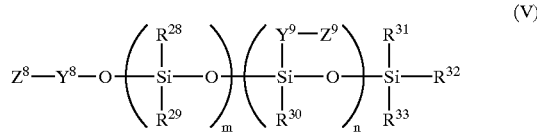

(V)

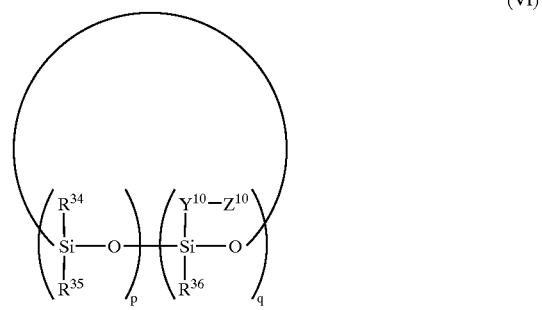

(VI)

(VII)

where each $R^{1-38}$ is independently at each occurrence a hydrogen atom, $C_{1-22}$ alkyl, $C_{1-22}$ alkoxy, $C_{2-22}$ alkenyl, $C_{6-14}$ aryl, $C_{6-22}$ alkyl-substituted aryl, $C_{6-22}$ aralkyl, $C_{1-22}$ fluoroalkyl, $C_{1-22}$ polyether, or $C_{1-22}$ amino alkyl; Z, $Z^{1-10}$, is independently at each occurrence, is a molecular hook; and Y, $Y^{1-10}$, independently at each occurrence, is a linker, wherein "m" in each formula has a value in a range between about 0 and about 13,000; "n" in each formula has a value in a range between about 0 and about 13,000 with the proviso that in formula (II) "n" is not 0; "m+n" in each formula has a value in a range between about 1 and about 26,000; "q" has a value of at least one "p+q" has a value of at least 3; "a" has a value greater than or equal to one; and "b" and "g" have a value of at least one.

10. The composition in accordance with claim 9 comprising at least one compound of formulas (I), (II), (III), (IV), or (V) wherein $R^{1-33}$ is methyl; "m" in each formula has a value in a range between about 20 and about 120; "n" in each formula has a value in a range between about 2 and about 10; and "m+n" in each formula has a value in a range between about 15 and about 120.

11. The composition in accordance with claim 9 comprising at least one compound of formula (VI), wherein "q" has a value of at least one; "p+q" has a value in a range between about 3 and about 6; and $R^{34-36}$ is methyl.

12. The composition in accordance with claim 9, wherein the moiety Z-Y is prepared by a process which comprises combining a hook with a linker precursor comprising a linker and a leaving group.

13. The composition in accordance with claim 12, wherein the leaving group is selected from the group consisting or chloride, bromide, iodide, tosylate, mesylate, phosphate, and cyclic leaving groups containing at least one heteroatom.

14. The composition in accordance with claim 13, wherein the leaving group is iodide, chloride, or bromide.

15. The composition in accordance with claim 1, wherein the linker comprises a $C_1$–$C_{100}$ alkyl, aryl, or alkylaryl group optionally containing one or more heteroatoms.

16. The composition in accordance with claim 15, wherein the linker comprises at least one compound of the formula (IX), (X), (XI), (XII), (XIII), (XIV), or (XV):

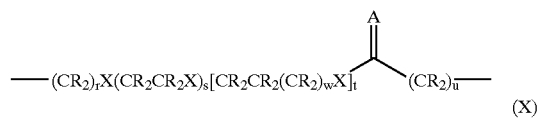
(IX)

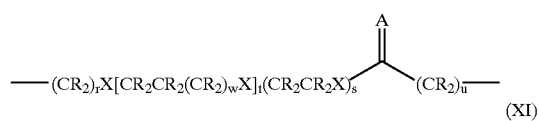
(X)

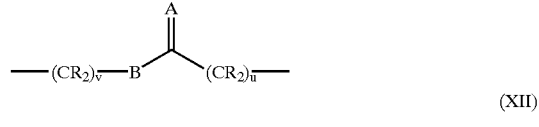
(XI)

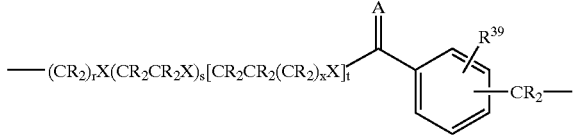
(XII)

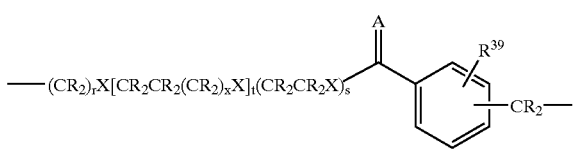
(XIII)

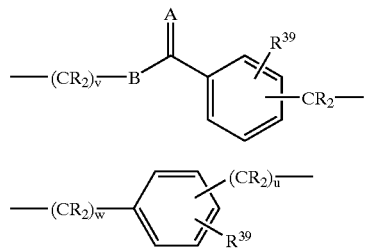
(XIV)

(XV)

where
r is in a range between about 1 and about 10;
s is in a range between about 0 and about 100;
t is in a range between about 0 and about 100;
u is in a range between about 1 and about 10;
v is in a range between about 1 and about 10;
w is 1 or 2;
x is 1 or 2;
X is O, NOH, NOR, or NR;
wherein R is independently at each occurrence hydrogen (H), $C_{1-22}$ alkyl, $C_{1-22}$ alkoxy, $C_{2-22}$ alkenyl, $C_{6-14}$ aryl, $C_{6-22}$ alkyl-substituted aryl, or $C_{6-22}$ aralkyl where the C can be unsubstituted or substituted with heteroatoms such as oxygen (O), nitrogen (N), sulfur (S) or halogen;
wherein $R^{39}$ is independently at each occurrence hydrogen (H), $C_{1-22}$ alkyl, $C_{1-22}$ alkoxy, $C_{2-22}$ alkenyl, $C_{6-14}$ aryl, $C_{6-22}$ alkyl-substituted aryl, $C_{6-22}$ aralkyl, or fused ring system which may or may not be fused to the phenyl group where the C can be unsubstituted or substituted with heteroatoms such as O, N, S or halogen;
A is O, NOH, NOR, NR or S;
B is O, NOH, NOR, NR or S; and
where the polysiloxane or the silicone resin is bound to the $(CR_2)_r$(Formula IX, X, XII, and XIII), $(CR_2)_v$ (Formula XI and XIV), or $(CR_2)_w$(Formula XV).

17. The composition in accordance with claim 16, wherein r is 2 or 3; s is in a range between about 4 and about 20; t is 0; u is 1; v is 2 or 3; w is 1 or 2; x is 1 or 2; X is O; R is H; $R^{39}$ is H; A is O; and B is O.

* * * * *